Aug. 26, 1941. C. J. VAN BOURGONDIEN Plant Pat. 486
FREESIA PLANT
Filed April 29, 1941
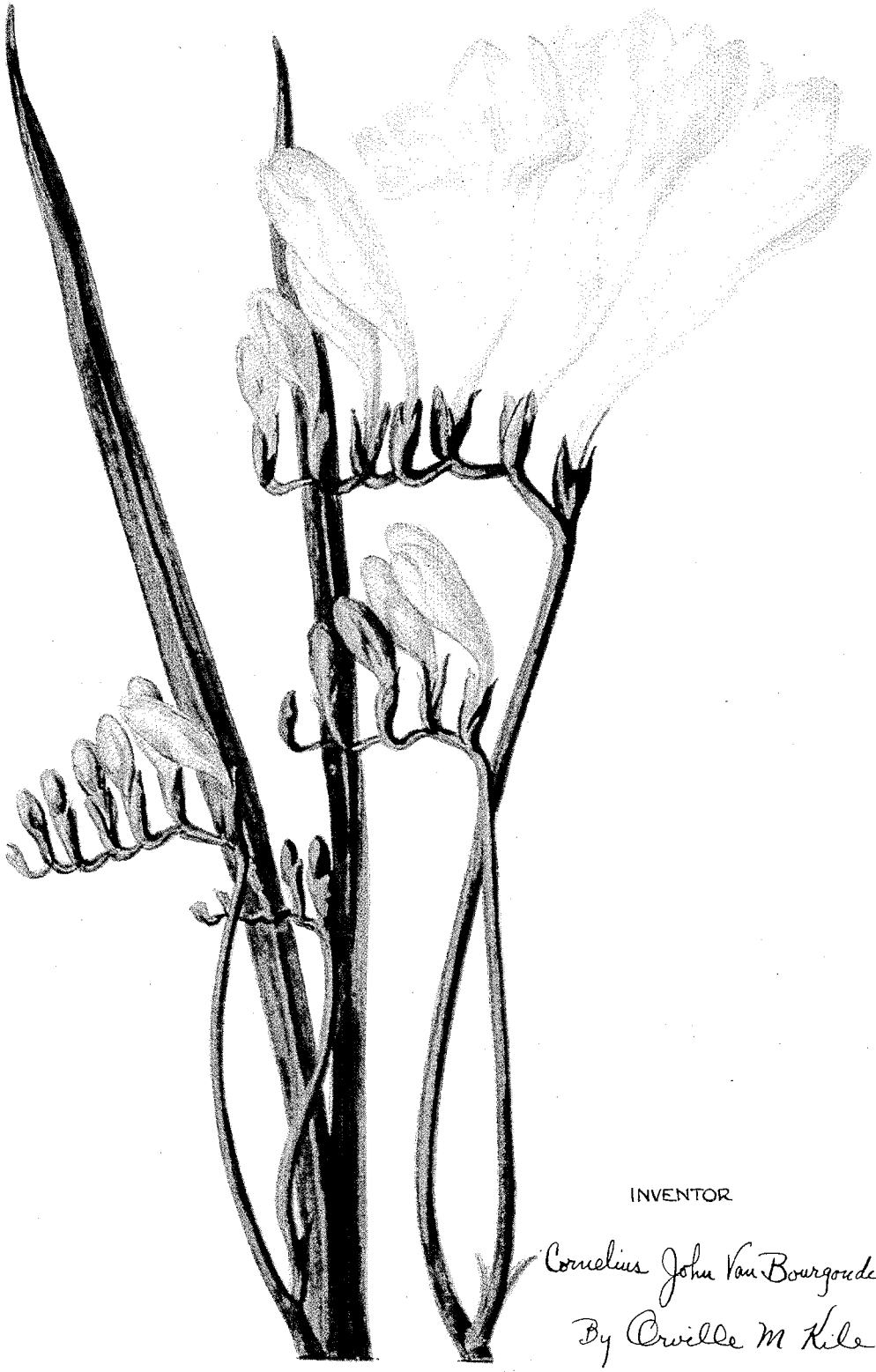
INVENTOR
Cornelius John Van Bourgondien
By Orville M Kile
PLANT PATENT AGENT Patented Aug. 26, 1941

Plant Pat. 486

UNITED STATES PATENT OFFICE

486

FREESIA PLANT

Cornelius John Van Bourgondien, Babylon, N. Y., assignor to C. J. Van Bourgondien, Inc., Babylon, N. Y.

Application April 29, 1941, Serial No. 391,009

1 Claim. (Cl. 47—60)

My new invention relates to improvements in freesia varieties and falls in the class known as giant freesias. The principal object of my invention is to produce a freesia variety of the giant type which has a sturdy and vigorously growing plant with delicately tinted blossoms of good substance.

My new variety is the result of definite breeding efforts carried on by me at my greenhouses. It is a seedling with Penserose Pink as its pollen parent and Albatre Supreme as its seed parent. It has been asexually reproduced for several years and its principal characteristics have proved to be permanently fixed.

While the color combination and size of the blossom are the most outstanding features of this new variety, other important distinguishing features are also evident. Good petal substance is very noticeable, this quality enabling its flowers to last a third longer than the flowers of the parent varieties and to ship exceptionally well. The foliage is narrower than that on most giant varieties and is very abundant. The long, sturdy flower stem is particularly well-branched.

The original illustration accompanying this application shows a blooming spike with several branches containing buds, together with some of the foliage—all in approximately natural colors and somewhat enlarged.

A detailed description of the plant and flower of this new freesia variety follows. Color plate references indicate Ridgway's Color Standards and Nomenclature.

*The plant*

Growth: Vigorous and upright; prolific in production of flowers; tall grower of giant type; produces very large number of corms (15 or 16), thus being capable of rapid reproduction. Plants from full-grown corms attain a height of 3 feet.

Stems: Tall; strong; upright; well-branched.

Corms: Unusually large both in size and number, often 15 or 16 produced to one plant.

Foliage: Very abundant; several spears in a cluster; tall, approximately 24 inches in height; unusually narrow for giant type; ¼ to ½ inch in width; midrib heavy; Parrot Green (Plate VI) to Spinach Green (Plate V).

*The flower*

Arrangement: Flowers are borne on long stems or spikes and are arranged in an upright position along a jointed rachis which is bent in such a manner that in general it appears to be at right angles to the stem. However, in most cases the first joint of the rachis is much longer than the other joints and arises from the stem at an acute angle, from which the remaining joints extend at a very obtuse angle, making the whole appear at right angles to the stem.

Sepals: Two; Parrot Green (Plate VI); long; somewhat clinging and sheath-like.

Form: Perianth long and tapering with only slightly constricted throat. Petals or lobes slightly overlapping. The spread of the petals is at something less than right angles but is sufficiently open to display the bright orange deep in the throat. Usually the central petal of what may be called the upper "lip" extends more nearly in a straight line than the others, while the petals of the lower "lip" are slightly smaller and drop open to a greater degree.

Size: Large; length 2½ to 2¾ inches; spread 2 to 2¼ inches.

Fragrance: Moderate and pleasing.

Petals: Broad; flat with little reflexing, folding or curling at edges; gently rounded at tip; very firm textured; somewhat uneven in size. Most often there are six petals or lobes but frequently there are eight.

Color: The greater portion of the flower is white but the tips and edges of the petals are tinted on both surfaces with delicate lavender rose. Upon opening of the flower this tint is from Pale Amaranth Pink to Rose Pink (Plate XII) with darker splotches of Rosolane Purple (Plate XXVI) to Amaranth Pink (Plate XII). As the blossom ages it assumes more of the purple tones, ranging through Pale Rosolane Purple, Amaranth Pink, and Light Mallow Purple (Plate XII). The upper portion of the petals of the dying flowers becomes approximately Mauve (Plate XXV). The constricted portion of the throat is golden yellow, between Light Cadmium (Plate IV) and deep Chrome (Plate III). This color is usually extended up the midrib of the petals of the lower "lip" and sometimes manifests itself as splotches on one or more of these petals. Because of the translucence of the throat, its color shows through with a dull yellow appearance.

Keeping quality: Excellent, due principally to the firm texture of the blossoms. This quality makes it an excellent shipper.

Reproductive organs:

*Stamens.*—Three. Filaments arise from the throat, are attached to the sides at their base, but are free for most of their length. They extend upward on the "upper" side of the perianth and are topped by gracefully curved stamens which extend almost perpendicular. Filaments are deep yellow at base, and white on the upper two-thirds of their length. Anthers are lavender above and white on their under side.

*Pistil.*—Compound, usually six-branched; arises from ovary and extends above stamens; free its entire length. Both styple and stigma are white.

Having thus disclosed my invention, I claim:

The new and distinct variety of giant freesia plant herein shown and described, characterized particularly by its large and vigorous growth; its prolific production of large corms; its abundant and very narrow foliage; its tall, strong, upright, well-branched flower stems; and its prolific production of very large flowers of particularly good substance, excellent keeping qualities and distinctive lavender pink tinting on white, as indicated.

CORNELIUS J. VAN BOURGONDIEN.